United States Patent [19]

Kühle et al.

[11] Patent Number: 4,513,003

[45] Date of Patent: Apr. 23, 1985

[54] PROCESS FOR PROTECTING WOOD USING N-(DICHLOROFLUOROMETHYLTHIO)-3,6-ENDOMETHYLENE-Δ⁴-TETRAHYDROPHTHALIMIDE

[75] Inventors: Engelbert Kühle, Bergisch-Gladbach; Erich Klauke, Odenthal; Wilfried Paulus; Hermann Genth, both of Krefeld, all of Fed. Rep. of Germany

[73] Assignee: Bayer Aktiengesellschaft, Leverkusen, Fed. Rep. of Germany

[21] Appl. No.: 399,632

[22] Filed: Jul. 19, 1982

[30] Foreign Application Priority Data

Aug. 7, 1981 [DE] Fed. Rep. of Germany ....... 3131250

[51] Int. Cl.³ .................... C07D 209/48; A61K 31/40
[52] U.S. Cl. ..................................... 514/411; 548/514
[58] Field of Search ......................... 548/514; 424/274

[56] References Cited

U.S. PATENT DOCUMENTS 2,553,770  5/1951  Kittleson ............................. 548/514
2,856,410  10/1958  Kittleson et al. .................... 548/514
3,499,030  3/1970  Kuhle et al. ........................ 548/514

FOREIGN PATENT DOCUMENTS 1193498  11/1980  Fed. Rep. of Germany .

OTHER PUBLICATIONS

H. Wollweber, Diels–Alder–Reaktion, Georg Thieme Verlag Stuttgart, 1972, p. 13.
R. Lukens, Jour. Agric. Food Chem. 14, 365 (1966).
Fette, Seifen Anstrichmittel 68, 275 (1966).

*Primary Examiner*—Nicholas S. Rizzo
*Attorney, Agent, or Firm*—Sprung Horn Kramer & Woods

[57] ABSTRACT

The novel N-(dichlorofluoromethylthio)-3,6-endomethylene-Δ⁴-tetrahydrophthalimides can be prepared from 3,6-endomethylene-Δ⁴-tetrahydrophthalimide with dichlorofluoromethanesulphenyl chloride in the presence of an acid-binding agent in solution. They can be used as microbicidal agents.

2 Claims, No Drawings

PROCESS FOR PROTECTING WOOD USING N-(DICHLOROFLUOROMETHYLTHIO)-3,6-ENDOMETHYLENE-Δ⁴-TETRAHYDROPHTHALIMIDE

The present invention relates to the novel compound N-(dichlorofluoromethylthio)-3,6-endomethylene-Δ⁴-tetrahydrophthalimide, a process for its preparation and its use as a microbicidal agent.

The use of N-(trihalogenomethylthio)-compounds for the protection of industrial materials against microbial degradation is known (U.S. Pat. No. 2,553,770, Journ. Agr. Food Chem. 14, 365 (1966), Fette, Seifen, Anstrichmittel 68, 275 (1966)). However, they are not always satisfactory because they are poorly soluble, particularly in some coating and impregnating agents.

N-(Dichlorofluoromethylthio)-3,6-endomethylene-Δ⁴-tetrahydrophthalimide has been discovered. The novel N-(dichlorofluoromethylthio)-3,6-endomethylene-Δ⁴-tetrahydrophthalimide can be in the form of two different isomers within the scope of the present invention.

The novel N-(dichlorofluoromethylthio)-3,6-endomethylene-Δ⁴-tetrahydrophthalimide has outstanding microbicidal properties and shows good solubility, particularly in coating and impregnating agents.

Within the scope of the present invention, the N-(dichlorofluoromethylthio)-3,6-endomethylene-Δ⁴-tetrahydrophthalimide can be substituted by customary radicals. Examples of customary radicals which may be mentioned are lower alkyl radicals ($C_1$ to about $C_6$), such as, for example, methyl and ethyl, and halogen such as, for example, fluorine and bromine.

The novel N-(dichlorofluoromethylthio)-3,6-endomethylene-Δ⁴-tetrahydrophthalimide of the formula (I)

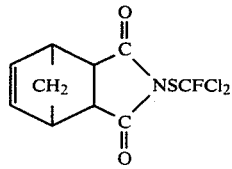

(I)

can be prepared by reacting 3,6-endomethylene-Δ⁴-tetrahydrophthalimide of the formula (II)

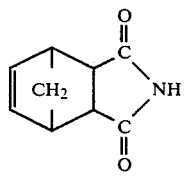

(II)

with dichlorofluoromethanesulphenyl chloride of the formula

Cl₂FSCl in the presence of an acid-binding agent in solution.

The 3,6-endomethylene-Δ⁴-tetrahydrophthalimide to be used as the starting material is known and may be prepared in a simple manner from ammonia and 3,6-endomethylene-Δ⁴-tetrahydrophthalic anhydride which is available by diene synthesis from cyclopentadiene and maleic anhydride. Depending on the temperature chosen, the compound is in the exo or endo form (H. Wollweber, Diels-Alder-Reaktion, Georg Thieme Verlag Stuttgart, 1972, page 13).

Examples of useful acid-binding agents for the process according to the invention are sodium hydroxide, sodium carbonate, triethylamine or pyridine.

Examples of useful solvents for the process according to the invention are hydrocarbons, such as, for example, toluene, chlorinated hydrocarbons, such as, for example, chlorobenzene, ethers such as, for example, dioxane, or water.

The process according to the invention is generally carried out in the temperature range from 0° to 100° C., preferably from 20° to 50° C.

The process according to the invention is generally carried out at atmospheric pressure.

The N-(dichlorofluoromethylthio)-3,6-endomethylene-Δ⁴-tetrahydrophthalimide according to the invention can be used as an active agent to combat microorganisms, in particular in industrial materials.

Industrial materials are inanimate materials, which have been manufactured for use in industry. Suitable examples of industrial materials which are to be protected from microbial alteration and damage by the active agent according to the invention are adhesives, glues, papers and cardboards, textiles, leather, wood, coating agents, building materials, rubber and plastic articles, cooling lubricants and other materials which can be decomposed by micro-organisms. Within the scope of materials to be protected, there may be mentioned parts of production plants, for example cooling water circulations, which can be adversely affected by micro-organisms. Industrial materials within the scope of the present invention which may preferably be mentioned are coating and impregnating agents for wood.

Examples of micro-organisms which can bring about degradation or alteration of the industrial materials are bacteria, fungi, yeasts, algae, slimes and viruses. The N-(dichlorofluoromethylthio)-3,6-endomethylene-Δ⁴-tetrahydrophthalimide according to the invention preferentially acts against mould fungi, and fungi which discolour and damage wood (Basidiomycetes).

Examples of micro-organisms which may be mentioned are those of the following species: Alternaria, such as *Alternaria tenuis*; Aspergillus, such as *Aspergillus niger*; Chaetomium, such as *Chaetomium globosum*; Coniophora, such as *Coniophora cerebella*; Lentinus, such as *Lentinus tigrinus*; Penicillium, such as *Penicillium glaucum*; Polyporus, such as *Polyporus versicolor*; Pullularia, such as *Pullularia pullulans*; Sclerophoma, such as *Sclerophoma pityophila*; Trichoderma, such as *Trichoderma viride*; Escherichia, such as *Escherichia coli*; and Staphylococcus, such as *Staphylococcus aureus*.

Depending on the area of application, the active agent according to the invention can be converted into the customary formulations, such as solutions, emulsions, suspensions, proofers, pastes and granules. These can be prepared in a manner known in itself, for example, by mixing the active agents with a diluent, which consists of a liquid solvent and/or solid carriers, if appropriate using surface-active agents, such as emulsifiers and/or dispersing agents and in the case where, for example, extenders are used, organic solvents can be used as auxiliary solvents if necessary. Organic solvents for the active agent according to the invention may be, for example, alcohols, such as lower aliphatic alcohols ($C_1$ to about $C_6$), preferably ethanol or isopropanol, ketones such as acetone or methyl ethyl ketone, liquid hydrocarbons, such as petroleum fractions, and chlorinated hydrocarbons, such as 1,2-dichloroethane.

Compositions wherein the N-(dichlorofluoromethylthio)-3,6-endomethylene-$\Delta^4$-tetrahydrophthalimide is present contain said compound in a concentration of 100 to 5, preferably 90 to 10, percent by weight.

The concentration in which the active agent according to the invention is used depends on the type and occurrence of the micro-organisms which are to be combated, as well as on the composition of the material to be protected. The optimum amount to be applied can be found using test series. Generally, the concentration for use is in the range from 0.001 to 5% by weight, preferably from 0.1 to 1.0% by weight, relative to the material to be protected.

The novel active agent according to the invention can also be in the form of a mixture with other known active agents. Examples of active agents which may be mentioned are the following: benzimidazolyl methylcarbamate, tetramethylthiuram disulphide, zinc dimethyldithiocarbamate, N-fluorodichloromethylthiophthalimide and N,N-dimethyl-N'-phenyl-(N'-fluorodichloromethylthio)-sulphamide, N-methylolamides and phenol derivatives, such as p-chloro-m-cresol, 2-phenylphenol and (2,2'-dihydroxy-5,5'-dichloro)-diphenylmethane.

PREPARATION EXAMPLE

Example 1

82 g (0.5 mol) of 3,6-endomethylene-$\Delta^4$-tetrahydrophthalimide (melting point 184°–186° C.) and 85 g (0.5 mol) of dichlorofluoromethanesulphenyl chloride in 400 ml cyclohexane are initially introduced. 56 g (0.55 mol) of triethylamine are added dropwise, and the temperature is allowed to rise to about 50° C. The mixture is then stirred for a short time and the reaction product and the precipitated triethylamine hydrochloride are filtered off at room temperature with suction. The crystals are washed with water and, after drying at 50° to 60° C., 112 g=75% of theory of the reaction product are obtained. Melting point 102°–104° C.

USE EXAMPLES

Example 2

To demonstrate the effectiveness against fungi, the minimum inhibitory concentrations (MIC) of the substance according to the invention are determined:

An agar prepared from beer wort and peptone is mixed with the substance according to the invention at concentrations from 0.5 mg/l to 5,000 mg/l.

After solidification of the agar, contamination with pure cultures of the test organisms listed in the table is carried out. After storage for 2 weeks at 28° C. and 60 to 70% relative atmospheric humidity, the MIC is determined. The MIC is the lowest concentration of active agent with which no growth by the type of microbe used ensues; it is given in the table below.

TABLE I

Details of the MIC values in mg/l relating to the effect on fungi of the active agents given below.

Active agent A: N—(Dichlorofluoromethylthio)-3,6-endomethylenetetrahydrophthalimide;
Active agent B: N,N—Dimethyl-N'—phenyl-N'—(dichlorofluoromethylthio)-sulphamide;
(Comparison)

| Test fungi | Active agent A | Active agent B |
|---|---|---|
| Alternaria tenuis | 10 | 20 |
| Aspergillus niger | 200 | 50 |
| Cladosporium herbarum | 7 | 35 |
| Coniophora cerebella | <1 | 10 |
| Paecilomyces varioti | 10 | 20 |
| Penicillium citrinum | 7 | 150 |
| Penicillium glaucum | 10 | 35 |
| Pullularia pullulans | 5 | 20 |
| Stachybotris atra C. | 15 | 50 |
| Trichoderma viride | 200 | 5,000 |

Example 3

(Action against bacteria)

An agar, containing bouillon as a nutrient medium, is treated with the active agents A and B (Example 2) given in Table II at concentrations from 1 to 5,000 ppm. The nutrient medium is then inoculated with either Escherichia coli or Staphylococcus aureus and the inoculated medium is maintained for 2 weeks at 28° C. and 60 to 70% relative atmospheric humidity. The MIC is the lowest concentration of active agent with which no growth by the type of microbe used ensues.

The MIC values are given in Table II.

TABLE II

Details of the MIC values in mg/l relating to the effect on bacteria of the active agents given below.

| | Active agent MIC (mg/l) A | MIC (mg/l) B |
|---|---|---|
| Escherichia coli | 200 | 500 |
| Staphylococcus aureus | 100 | 5,000 |

Example 4

The following table shows that the N-(dichlorofluoromethylthio)-3,6-endomethylene-$\Delta^4$-tetrahydrophthalimide (substance A) according to the invention has very good solubility properties, particularly when compared to the usual commercial product N,N-dimethyl-N'-phenyl-N'-(dichlorofluoromethylthio)-sulphamide (substance B). The surprisingly good solubility properties combined with the superior effectiveness of the substance according to the invention facilitate the use in coating and impregnating agents in a manner which is technically progressive.

Solubility of substance A compared to substance B (g/l at 20° C.):

| Solvent | A | B |
|---|---|---|
| Ethyl acetate | 330 | 117 |
| Solvesso 100 | 200 | 75 |
| Shellsol AB | 140 | 60 |
| Xylene | 250 | 65 |

What is claimed is:

1. A process for protecting wood against microbial alteration or damage by a microorganism which comprises applying to said wood a microbicidally effective amount of N-(dichlorofluoromethylthio)-3,6-endomethylene-$\Delta^4$-tetrahydrophthalimide.

2. A process according to claim 1, wherein said N-(dichlorofluoromethylthio)-3,6-endomethylene-$\Delta^4$-tetrahydrophthalimide is applied to said wood in an amount of 0.001 to 5% by weight relative to said wood.

* * * * *